(12) United States Patent
Shin et al.

(10) Patent No.: US 11,642,006 B2
(45) Date of Patent: May 9, 2023

(54) DETACHABLE ENDOSCOPE WITH ADJUSTABLE BENDING ANGLE

(71) Applicant: TAEWOONG MEDICAL CO., LTD., Gimpo-si (KR)

(72) Inventors: Kyong Min Shin, Gyeonggi-do (KR); Sung Hwan Park, Gimpo-si (KR); Hyun Soo Ji, Gimpo-si (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 284 days.

(21) Appl. No.: 17/014,118

(22) Filed: Sep. 8, 2020

(65) Prior Publication Data

US 2021/0068624 A1 Mar. 11, 2021

(30) Foreign Application Priority Data

Sep. 11, 2019 (KR) .......................... 10-2019-0112952

(51) Int. Cl.
*A61B 1/00* (2006.01)
*A61B 1/005* (2006.01)
(Continued)

(52) U.S. Cl.
CPC ........ *A61B 1/00105* (2013.01); *A61B 1/0052* (2013.01); *A61B 1/05* (2013.01);
(Continued)

(58) Field of Classification Search
CPC ..... A61B 1/00105; A61B 1/0052; A61B 1/05; A61B 1/0051
See application file for complete search history.

(56) References Cited

U.S. PATENT DOCUMENTS 4,203,430 A * 5/1980 Takahashi ............ A61B 1/0052
600/149
2008/0125628 A1 * 5/2008 Ueno ................... A61B 1/0052
600/130
(Continued)

FOREIGN PATENT DOCUMENTS

| KR | 10-0673412 B1 | 1/2007 |
| KR | 10-1091999 B1 | 12/2011 |
| KR | 10-1783225 B1 | 9/2017 |

*Primary Examiner* — Anh Tuan T Nguyen
*Assistant Examiner* — Rynae E Boler
(74) *Attorney, Agent, or Firm* — Bridgeway IP Law Group, PLLC; Jihun Kim

(57) ABSTRACT

A detachable endoscope includes: an operation part for operating the front end of an insertion part having a lighting photographing part to be bent and a detachable unit for detachably coupling the operation part and the insertion part, wherein the detachable unit includes: a first detachable module connected to first, second, third, and fourth operation wires arranged parallel to each other so that the respective one ends are connected to the front end inside the insertion part and provided on the rear end of the insertion part, a second detachable module connected to first, second, third, and fourth connection wires of a direction conversion part for converting a rotational motion into a linear motion in the operation part and provided on the front end of the operation part, and a bending control part for adjusting an angle at which the front end of the insertion part is bent and displaced vertically or horizontally.

9 Claims, 11 Drawing Sheets

(51) Int. Cl.
*A61B 1/05* (2006.01)
*A61B 1/06* (2006.01)
A61B 1/12 (2006.01)
A61B 1/273 (2006.01)
A61B 1/31 (2006.01)

(52) U.S. Cl.
CPC ............... *A61B 1/06* (2013.01); *A61B 1/126* (2013.01); *A61B 1/2736* (2013.01); *A61B 1/31* (2013.01)

(56) References Cited

U.S. PATENT DOCUMENTS

| | | | |
|---|---|---|---|
| 2013/0190567 A1* | 7/2013 | Miyoshi | G02B 23/2476 600/137 |
| 2017/0209227 A1* | 7/2017 | Yoshimura | A61B 34/30 |

\* cited by examiner

DETACHABLE ENDOSCOPE WITH ADJUSTABLE BENDING ANGLE

TECHNICAL FIELD

The present disclosure relates to an endoscope, and more specifically, to a detachable endoscope with an adjustable bending angle, which may easily couple and use an operation part for operating the front end of an insertion part inserted into a body to be bent and the insertion part upon endoscopic surgery, and easily separate the operation part and the insertion part to store or disinfect the operation part and the insertion part after the endoscopic surgery to reuse them, and easily adjust an angle at which the front end of the insertion part is bent and displaced according to endoscopic surgery environments to give a multi-function to equipment.

BACKGROUND ART

Generally, in a surgery using an endoscope, a camera-installed endoscope and a surgical tool are inserted through a small hole without largely incising a human body, and then the surgery is conducted while examining a patient's affected area through the image photographed by the endoscope in a body.

Particularly, the endoscopic surgery starting from laparoscopic surgery has an advantage in that the scar area is small and the bleeding is also less because an incision site is small compared to laparotomy, so that a recovery time of the patient is short after the surgery.

Recently, not only the technology has been developed to enable the endoscopic surgery for almost all surgeries requiring laparotomy, but also the endoscopic surgery is increasingly applied in other medical fields.

A conventional general endoscope is integrally composed of an insertion part inserted into the human body and an operation part for controlling the insertion part, and a plurality of pipelines and guides are embedded therein through the inside of each part, and particularly, since an imaging element such as an expensive CCD or the like is provided on the front end of the insertion part inserted into the body, there is a problem in that it is difficult to separate only the insertion part from the operation part to be replaced with new one.

In addition, as such an endoscope, a gastric endoscope for confirming or removing the polypus of the lesion site while observing the inner wall of the stomach with the large inner width, and a colonofiberscope for confirming or removing the polypus of the lesion site while observing the inner wall of the large intestine with the small inner width and many bending portions are used selectively.

In the gastric endoscope, since the front end of an insertion part having a lighting photographing part enters the internal space of the stomach in the body from the top to the bottom through the patient's mouth, and then the front end of the insertion part observes the inner wall which forms a wide internal space in width, a bending angle for displacing the front end of the insertion part by operating the front end of the insertion part to be bent vertically and horizontally by the rotational operation of an operation part is designed to be largely set as about 180 degrees to 210 degrees or more so that the front end of the insertion part facing downward may be bent to a rear side which is opposite to a proceeding direction.

On the other hand, in the colonofiberscope, since the front end of an insertion part with a lighting photographing part enters the internal space of the large intestine of the body from the bottom to the top through the anus, which is the end of the large intestine of the patient, and then the front end of the insertion part observes the inner wall which forms a very narrow internal space in width, the bending angle for displacing the front end of the insertion part by operating the front end of the insertion part to be bent vertically and horizontally is designed to be set as about 100 degrees to 180 degrees or less to be relatively small compared to that of the gastric endoscope.

(Patent Document 1) KR10-0673412B1
(Patent Document 2) KR10-1091999B1
(Patent Document 3) KR10-1783225B1

Patent Documents 1 to 3 disclose various types of detachable endoscopes which may couple and use the insertion part inserted into the body and the operation part for operating the insertion part or separate and store the insertion part and the operation part according to the trend of further strengthening the hygiene function of the endoscope used for medical use in recent years.

However, since the detachable endoscopes disclosed in these Patent Documents may not interchangeably use the insertion part for the dedicated gastric endoscope designed so that the bending angle is largely set and the insertion part for the dedicated colonofiberscope designed so that the bending angle is set relatively small in common, the detachable endoscope dedicated to the stomach and the detachable endoscope dedicated to the large intestine are provided, respectively, thereby increasing a maintenance cost, and increasing a purchase cost of the endoscope equipment due to the purchase of multiple equipment according to the use of endoscopic surgery.

DISCLOSURE

Technical Problem

Therefore, the present disclosure is intended to solve the aforementioned problems, and an object of the present disclosure is to provide a detachable endoscope with an adjustable bending angle, which may easily vary a bending angle at which the front end of an insertion part is bent vertically and horizontally by a simple operation using a tool according to endoscopic surgery conditions, thereby performing a gastric endoscopic surgery function and a colonofiberscope surgery function using one insertion part.

The objects to be achieved in the present disclosure are not limited to the aforementioned object, and other objects not mentioned will be clearly understood by those skilled in the art to which the present disclosure pertains from the following description.

Technical Solution

As a specific means for achieving the objects, a preferred exemplary embodiment of the present disclosure provides a detachable endoscope with an adjustable bending angle including an operation part for operating the front end of an insertion part having a lighting photographing part to be bent and a detachable unit for detachably coupling the operation part and the insertion part, in which the detachable unit includes: a first detachable module connected to the first, second, third, and fourth operation wires arranged parallel to each other so that the respective one ends are connected to the front end inside the insertion part and provided on the rear end of the insertion part, a second detachable module connected to first, second, third, and fourth connection wires of a direction conversion part for converting a rotational motion into a linear motion in the operation part and provided on the front end of the operation part, and a bending control part for adjusting an angle at which the front end of the insertion part is bent and displaced vertically or horizontally, the first detachable module includes: a first module main body having first, second, third, and fourth linear guide holes formed to penetrate the insides thereof in a longitudinal direction, and having a central placement hole formed to penetrate the inside thereof in a thickness direction, first, second, third, and fourth rack gears having the one ends correspondingly connected to the respective ends of the first, second, third, and fourth operation wires and assembled in the first, second, third, and fourth linear guide holes, a first pinion gear gear-engaged between the first and second rack gears, a second pinion gear gear-engaged between the third and fourth rack gears, and a gear shaft having the first and second pinion gears assembled with a vertical predetermined interval and fixedly installed in the central placement hole, and the bending control part includes: a first adjustment part for controlling linear movement distances of the first and second rack gears reciprocating through the first and second linear guide holes to vary the vertical bending angle of the front end of the insertion part, and a second adjustment part for controlling linear movement distances of the third and fourth rack gears reciprocating through the third and fourth linear guide holes to vary the horizontal bending angle of the front end of the insertion part.

At this time, the first adjustment part may include: a first upper fixing block for rotatably supporting the respective one ends of first and second control shafts having predetermined lengths disposed parallel to the first and second rack gears, a second upper fixing block for rotatably supporting the respective other ends of the first and second control shafts, and first and second stoppers assembled in the first and second control shafts to be movable in location so that one ends thereof are located on movement paths of first and second movable bodies moved with the first and second rack gears.

At this time, the first and second stoppers may include: protrusions formed to protrude from one side ends of the respective main bodies screw-coupled to outer surfaces of the first and second control shafts so as to contact the first and second movable bodies reciprocating along first and second linear-type slits of the first module main body.

At this time, the respective one side ends of the first and second control shafts may have straight or cross-shaped grooves so as to facilitate a locking rotational operation by a tool.

At this time, the first adjustment part may include: an upper auxiliary block having first and second guide holes, in which the respective one ends of the first and second control shafts enter to be disposed, formed to penetrate the inside thereof, the first and second guide holes.

At this time, the second adjustment part includes: a first lower fixing block for rotatably supporting the respective one ends of third and fourth control shafts having predetermined lengths disposed parallel to the third and fourth rack gears, a second lower fixing block for rotatably supporting the respective other ends of the third and fourth control shafts, and third and fourth stoppers assembled in the third and fourth control shafts to be movable in location so that one ends thereof are located on movement paths of third and fourth movable bodies moved with the third and fourth rack gears.

At this time, the third and fourth stoppers include: protrusions formed to protrude from one side ends of the respective main bodies screw-coupled to outer surfaces of the third and fourth control shafts so as to contact the third and fourth movable bodies reciprocating along third and fourth linear-type slits of the first module main body.

At this time, the respective one side ends of the third and fourth control shafts have straight or cross-shaped grooves so as to facilitate a locking rotational operation by a tool.

At this time, the second adjustment part includes: a lower auxiliary block having third and fourth guide holes, in which the respective one ends of the third and fourth control shafts enter to be disposed, formed to penetrate the inside thereof.

Advantageous Effects

The preferred exemplary embodiment of the present disclosure described above has the following effects.

It is possible to easily vary the maximum value of the bending angle at which the front end of the insertion part is bent vertically and horizontally by the simple rotational operation using a tool and power according to the endoscopic surgery conditions such as the colonofiberscope surgery or the gastric endoscope surgery to simultaneously perform the gastric endoscope surgery function and the colonofiberscope surgery function using one insertion part, thereby saving the purchase cost of the endoscopic equipment, and reducing the number of endoscope equipment to save the maintenance cost according to disinfection, cleaning, and storage.

If the insertion part inserted into the human body is contaminated or the functional abnormality occurs, it is possible to separate this insertion part to easily replace the insertion part, thereby improving safety, and to discard the contaminated insertion part and mount a clean and new insertion part to be replaced therein, thereby safely performing the endoscopic surgery.

BEST MODE

Figure 1:
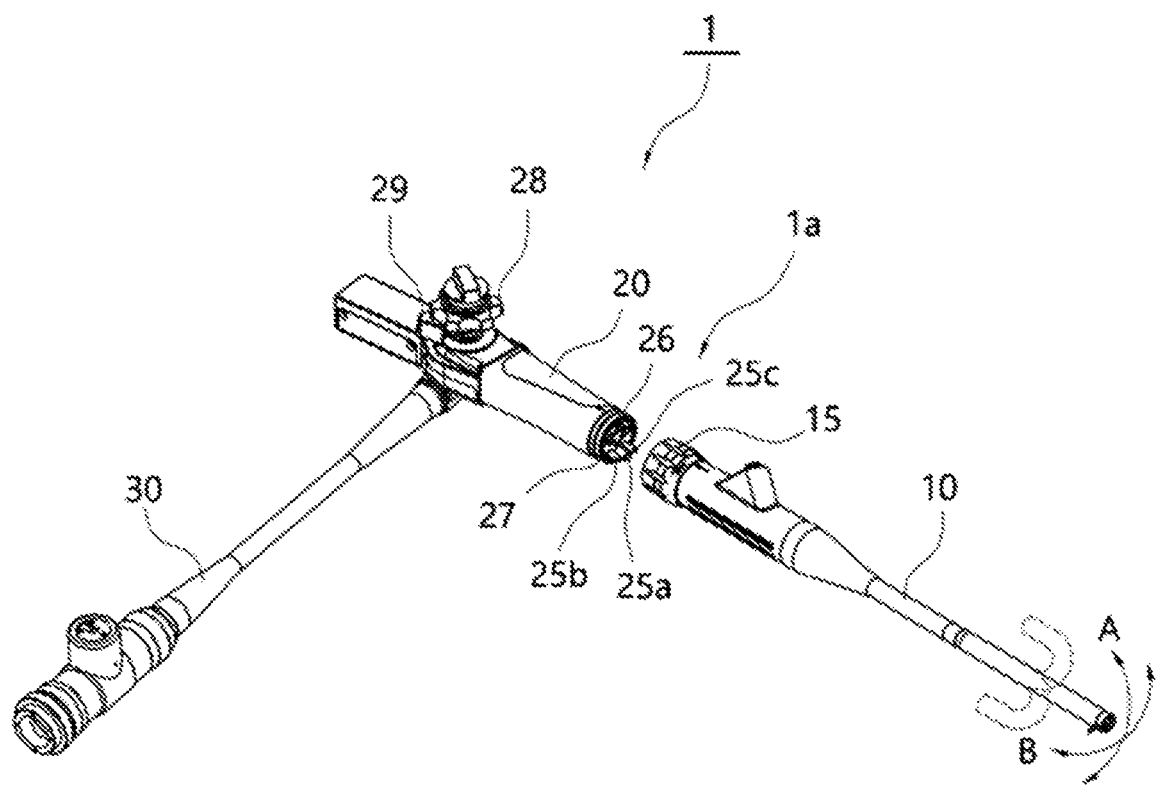
FIG. 1 is a perspective diagram illustrating an overall detachable endoscope with an adjustable bending angle according to an exemplary embodiment of the present disclosure.

Hereinafter, preferred exemplary embodiments of the present disclosure will be described in detail with reference to the accompanying drawings so that those skilled in the art to which the present disclosure pertains may easily practice the present disclosure. However, in specifically describing a structural principle of the preferred exemplary embodiments of the present disclosure, detailed descriptions of the related and known functions or components will be omitted if it is determined that the detailed descriptions thereof may unnecessarily obscure the gist of the present disclosure.

In addition, the same reference numerals are used for the parts having similar functions and operations throughout the drawings.

In addition, throughout the specification, when a part is said to be 'connected' to another part, the part is not only 'directly connected' to another part, but also 'indirectly connected' to another part with other elements interposed therebetween. In addition, the term 'including' a component means that other components may be further included, rather than excluding other components, unless specially stated otherwise.

As illustrated in FIG. 1, a detachable endoscope 1 according to an exemplary embodiment of the present disclosure includes an insertion part 10 having the front end inserted into a body upon endoscopic surgery, an operation part 20 having a plurality of operation handles, an universal joint 30 electrically connected to an endoscope control management system, and a detachable unit 1*a* for coupling the insertion part 10 to the operation part 20 to mechanically connecting the insertion part to the operation part before the endoscopic surgery or separating the insertion part 10 and the operation part 20 after the endoscopic surgery.

The insertion part 10 is made of a flexible tube material to adjust a direction inserted into the body, and has a lighting photographing part having a light source for illuminating the body and an image sensor for photographing the in-body on the front end thereof.

The operation part 20 has an upper operation handle 28 for operating the front end of the insertion part inserted into the body to be bent vertically and a lower operation handle 29 for operating the front end of the insertion part to be bent horizontally.

The inside of the operation part 20 has a direction conversion part which has upper and lower sprockets provided in the upper and lower operation handles, respectively, and upper and lower chains connected to the upper and lower sprockets to convert rotational motions of the upper and lower sprockets into linear motions of the upper and lower chains upon operations of the upper and lower operation handles, thereby converting the selective rotational motions of the upper and lower operation handles into the linear motions, and the upper and lower chains are connected to the inner end of the front end of the insertion part via a plurality of operation wires disposed inside the insertion part.

By converting some of the plurality of operation wires disposed in the insertion part into the linear motions through the upper and lower sprockets rotated by the selective rotations of the upper and lower operation handles by the user and the upper and lower chains which linearly reciprocate, the front end of the insertion part is bent vertically or horizontally in the body according to the linear motion of the operation wire.

The operation part has an operation switch and an operation button for putting or discharging liquid and gas for cleaning and disinfection upon endoscopic surgery, and the rear end of the insertion part detachably assembled with the front end of the operation part via the detachable unit is provided with a doorway through which a surgical element, such as an endoscopic treatment element having a clip, enters into and exits from the insertion part and a cap for opening and closing the doorway.

Figure 2:
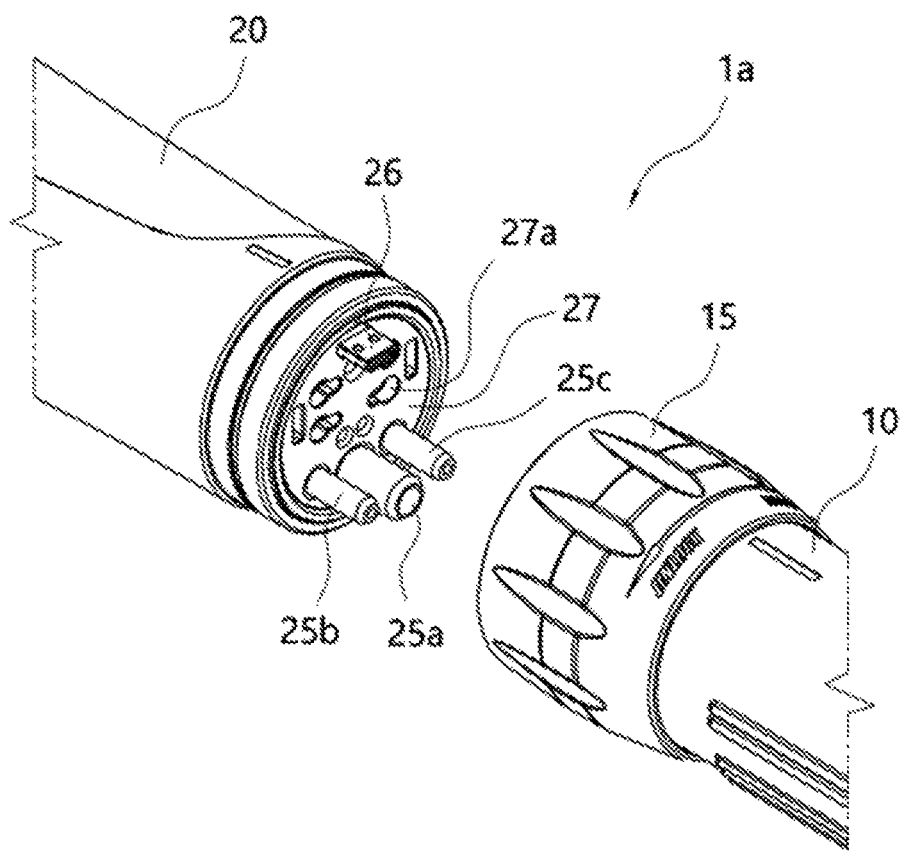
FIG. 2 is an enlarged diagram illustrating a coupling portion between an insertion part and an operation part of the detachable endoscope with the adjustable bending angle according to the exemplary embodiment of the present disclosure.

In FIGS. 1 and 2, an end cover 27 provided on the end of the operation part has an air supply channel 25*b* for supplying air, a water supply channel 25*c* for supplying water, and a suction channel 25*a* for sucking water and air to discharge the water and the air to the outside, and has a terminal 26 electrically connected to a lighting photographing part, whereas the rear end of the insertion part 10 made of a substantially cylindrical housing has a ring-type coupling body 15 screw-coupled to a female screw part formed on the front end of the operation part 20 formed of a cylindrical housing.

Figure 3:
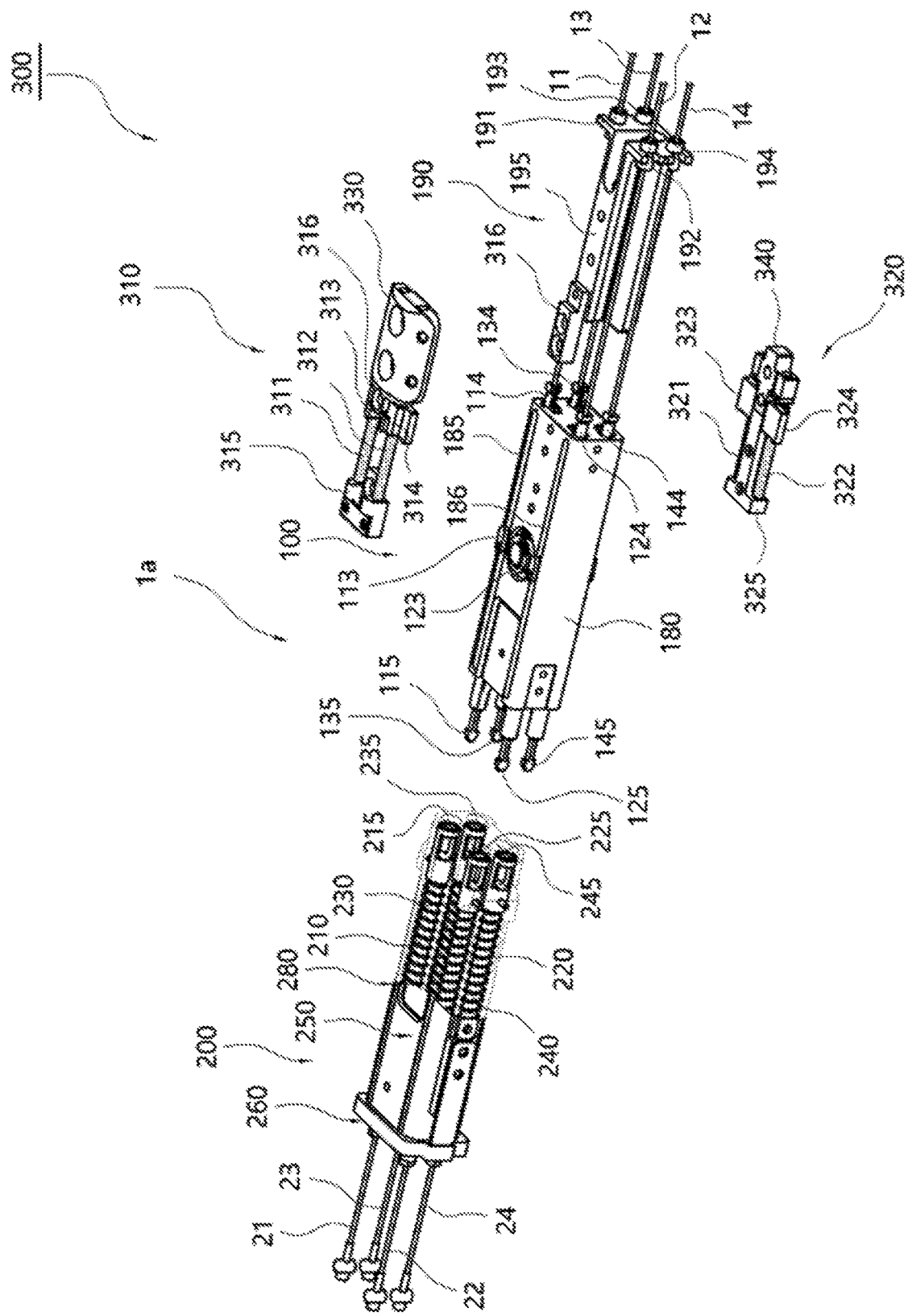
FIG. 3 is a perspective diagram illustrating a detachable unit provided in the detachable endoscope with the adjustable bending angle according to the exemplary embodiment of the present disclosure.

As illustrated in FIGS. 2 and 3, the detachable endoscope 1 according to the preferred exemplary embodiment of the present disclosure includes the detachable unit 1*a* for detachably coupling the rear end of the insertion part 10 and the front end of the operation part 20.

The detachable unit 1*a* includes a first detachable module 100 inserted into and disposed in the insertion part, a second detachable module 200 inserted into and disposed in the operation part and correspondingly coupled to the first detachable module, and a bending control part 300 for adjusting an angle at which the front end of the insertion part is bent vertically and horizontally according to surgery conditions and environments before operating endoscopic surgery.

The first detachable module 100 is connected to the respective one ends of first and second operation wires 11, 12 disposed inside the insertion part parallel to each other to operate the front end of the insertion part to be bent vertically (A), and connected to the respective one ends of third and fourth operation wires 13, 14 disposed inside the insertion part parallel to each other to operate the front end of the insertion part to be bent horizontally (B).

The second detachable module 200 is connected to both ends of each of the upper and lower chains wound around the upper and lower sprockets rotated forward and backward by the upper and lower operation handles 28, 29 via first, second, third, and fourth connection wires 21, 22, 23, 24.

Here, although it has been illustrated and described that the first and second connection wires 21, 22 connected to both ends of the upper chain wound around the upper sprocket operate the front end of the insertion part to be bent vertically in conjunction with a pair of the first and second operation wires 11, 12 disposed parallel to each other on the upper side inside the insertion part in the figure, whereas the third and fourth connection wires 23, 24 connected to both ends of the lower chain wound around the lower sprocket operate the front end of the insertion part to be bent horizontally in conjunction with the pair of the third and fourth operation wires 13, 14 disposed parallel to each other on the lower side inside the insertion part in the figure, the present disclosure is not limited thereto and the vertically and horizontally bending operation may be conversely performed according to the endoscope design.

In addition, although it has been illustrated and described that the rotations of the upper and lower sprockets are performed by the manual rotational operation of the worker gripping the upper and lower operation handles provided in the operation part, the rotations of the upper and lower sprockets are not limited thereto and may be performed by connecting a rotary shaft assembled with the upper and lower sprockets to a driving means such as a motor and using a separate remote operation means such as a joystick for controlling the driving means.

As illustrated in FIGS. 3, 4a, 4b, 5, 6, and 7, the first detachable module 100 includes first and second rack gears 110, 120 arranged on the upper side thereof, third and fourth rack gears 130, 140 arranged on the lower side thereof, a first pinion gear 150 disposed between the first and second rack gears, a second pinion gear 160 disposed between the third and fourth rack gears, a gear shaft 170 coupled to the first and second pinion gears 150, 160, and a first module main body 180 for accommodating the first and second rack gears, the third and fourth rack gears, the first pinion gear, and the second pinion gear therein.

The first module main body 180 is a block structure having a substantially cuboid shape which has first, second, third, and fourth linear guide holes 181, 182, 183, 184 formed to penetrate the insides of the bodies in a longitudinal direction and a central placement hole 189, which communicates with the first, second, third, and fourth linear guide holes in a thickness direction substantially perpendicular to the longitudinal direction, formed to penetrate the center of the body.

Outer surfaces of both sides of the first module main body 180 are opened by having both ends of the first, second, third, and fourth linear guide holes 181, 182, 183, 184 exposed, respectively, and the upper and lower surfaces of the first module main body 180 are opened by having both ends of the central placement hole 189 exposed.

The first and second rack gears 110, 120 are linear bar-type gear members which are connected to the respective one ends of the first and second operation wires 11, 12 arranged parallel to each other on the upper side inside the insertion part, and have the respective other ends of the first and second operation wires detachably coupled to the second detachable module, and the third and fourth rack gears 130, 140 are linear bar-type gear members which are connected to the respective one ends of the third and fourth operation wires 13, 14 arranged parallel to each other on the lower side inside the insertion part, and have the respective other ends of the third and fourth operation wires detachably coupled to the second detachable module.

The first pinion gear 150 is a gear member which is gear-engaged between the first rack gear 110 and the second rack gear 120 disposed parallel to each other, and thus linearly moves the first and second rack gears in opposite directions so as to operate the front end of the insertion part to be bent vertically upon rotational operation of the upper operation handle.

The second pinion gear 160 is a gear member which is gear-engaged between the third rack gear 130 and the fourth rack gear 140 disposed parallel to each other just below the first and second rack gears, and thus linearly moves the third and fourth rack gears in opposite directions so as to operate the front end of the insertion part to be bent horizontally upon rotational operation of the lower operation handle.

The first, second, third, and fourth rack gears 110, 120, 130, 140 are slidably assembled in the first, second, third, and fourth linear guide holes, include linear bars 111, 121, 131, 141 having predetermined lengths having both ends externally exposed to both sides of the first module main body 180, and include linear gear teeth 112, 122, 132, 142 having predetermined lengths which are formed on the linear bar and gear-engaged with circular gear teeth formed on the outer circumferential surfaces of the first and second pinion gears 150, 160.

Although it has been illustrated and described that the linear gear teeth 112, 122, 132, 142 are integrally provided on the outer surfaces of the linear bars of the first and second rack gears facing the first pinion gear, and the outer surfaces of the linear bars of the third and fourth rack gears facing the second pinion gear, respectively, they are not limited thereto and may be provided in an assembling type.

The linear gear teeth 112, 122, 132, 142 are exposed through communication holes 112a, 122a, 132a, 142a cutout to communicate the first, second, third, and fourth linear guide holes with the central placement hole, so that the first and second rack gears and the first pinion gear, and the third and fourth rack gears and the second pinion gear are gear-engaged with each other.

The first, second, third, and fourth linear guide holes 181, 182, 183, 184 may be composed of guide holes 181a, 182a, 183a, 184a having a substantially circular shape which are guided by the contact between the outer circumferential surfaces of the respective linear bars of the first, second, third, and fourth rack gears 110, 120, 130, 140 and the inner surfaces thereof and extension holes 181b, 182b, 183b, 184b extending from the guide holes to the outside so that the respective gear teeth of the first, second, third, and fourth rack gears 110, 120, 130, 140 are guided and moved without interference.

At this time, although it has been illustrated and described that the outer circumferential surfaces of the respective linear bars of the first, second, third, and fourth rack gears 110, 120, 130, 140 and the inner circumferential surfaces of the respective guide holes of the first, second, third, and fourth linear guide holes are entirely in contact with each other, the present disclosure is not limited thereto and may have a linear-type protrusion having a predetermined length in a guide direction on the outer circumferential surface of the linear bar or the inner circumferential surface of the guide hole so as to smoothly perform the linear guide movement while reducing the frictional resistance therebetween by partially contacting the outer circumferential surfaces of the respective linear bars of the first, second, third, and fourth rack gears 110, 120, 130, 140 with the inner circumferential surfaces of the respective guide holes of the first, second, third, and fourth linear guide holes to reduce contact areas.

The outer surfaces of both sides of the first module main body 180 corresponding to the first, second, third, and fourth rack gears 110, 120, 130, 140 are cutout to form linear-type guide slits 185, 186, 187, 188 therein, and the respective linear bars of the first, second, third, and fourth rack gears 110, 120, 130, 140 include movable bodies 113, 123, 133, 143 moving along the linear-type guide slits.

The movable bodies 113, 123, 133, 143 are detachably assembled in assembling grooves recessed in the centers of the lengths of the liner bars 111, 121, 131, 141 by fastening members, and the linear gear tooth and the movable body are preferably provided on the outer surface of the linear bar with a phase difference of about 90 degrees.

In addition, the respective one ends of the first, second, third, and fourth rack gears 110, 120, 130, 140 corresponding to the first, second, third, and fourth operation wires 11, 12, 13, 14 are connected to the respect one ends of the first, second, third, and fourth operation wires via a first buffer part 410 having a first buffer body connected thereto.

The respective other ends of the first, second, third, and fourth rack gears 110, 120, 130, 140 corresponding to the second detachable module 200 have first, second, third, and fourth connecting ports 115, 125, 135, 145 locked and connected to first, second, third, and fourth connected ports 215, 225, 235, 245 provided on the respective ends of the first, second, third, and fourth connection shafts 210, 220, 230, 240 provided in the second detachable module 200.

Here, it is possible to transfer powers selectively reciprocating the first, second, third, and fourth operation wires so as to operate the front end of the insertion part to be bent vertically and horizontally upon rotational operation by the upper and lower operation handles provided in the operation part by the locking-connection between the first, second, third, and fourth connecting ports 115, 125, 135, 145 of the first, second, third, and fourth rack gears 110, 120, 130, 140 and the first, second, third, and fourth connected ports 215, 225, 235, 245 of the first, second, third, and fourth connection shaft 210, 220, 230, 240.

The gear shaft 170 is a shaft member in which the first and second pinion gears 150, 160 gear-engaged with the first, second, third, and fourth rack gears 110, 120, 130, 140 are rotatably assembled with vertically predetermined intervals and correspondingly inserted into and fixedly installed to the central placement hole 189 of the first module main body.

The lower end of the gear shaft 170 is integrally provided with a plate bracket 173 assembled by a fastening member by contacting the outer surface of the first module main body while covering one end of the opening end of the central placement hole 189, and the upper end of the gear shaft is provided with a separation prevention clip 156 for preventing the first and second pinion gears from being separated to the outside.

A first cylindrical sleeve 155 is provided between the first pinion gear 150 and the separation prevention clip 156 to maintain the interval therebetween, and a second cylindrical sleeve 165 is also provided between the first pinion gear 150 and the second pinion gear 160 to maintain the interval therebetween.

The outer surfaces of the gear shaft 170 corresponding to the first and second pinion gears 150, 160 have first and second ring-type grooves recessed, respectively, and the first and second ring-type grooves are provided with first and second elastic rings 171, 172 made of a rubber material so that the inner circumferential surfaces and outer circumferential surfaces of the first and second pinion gears 150, 160 are elastically in contact with each other.

It is possible to reduce the occurrence of noise due to backlash caused by gear-engaging between the first and second rack gears 110, 120 and the first pinion gear 150, and between the third and fourth rack gears 130, 140 and the second pinion gear 160 by the elastic contact between the respective inner circumferential surface of the first and second pinion gears 150, 160 and the outer circumferential surfaces of the first and second elastic rings 171, 172, and to move the first and second rack gears linearly and more smoothly in opposite directions without using a lubricant and move the third and fourth rack gears linearly and more smoothly in opposite directions without using the lubricant when operating the front end of the insertion part to be bent vertically and horizontally.

Figure 4A:
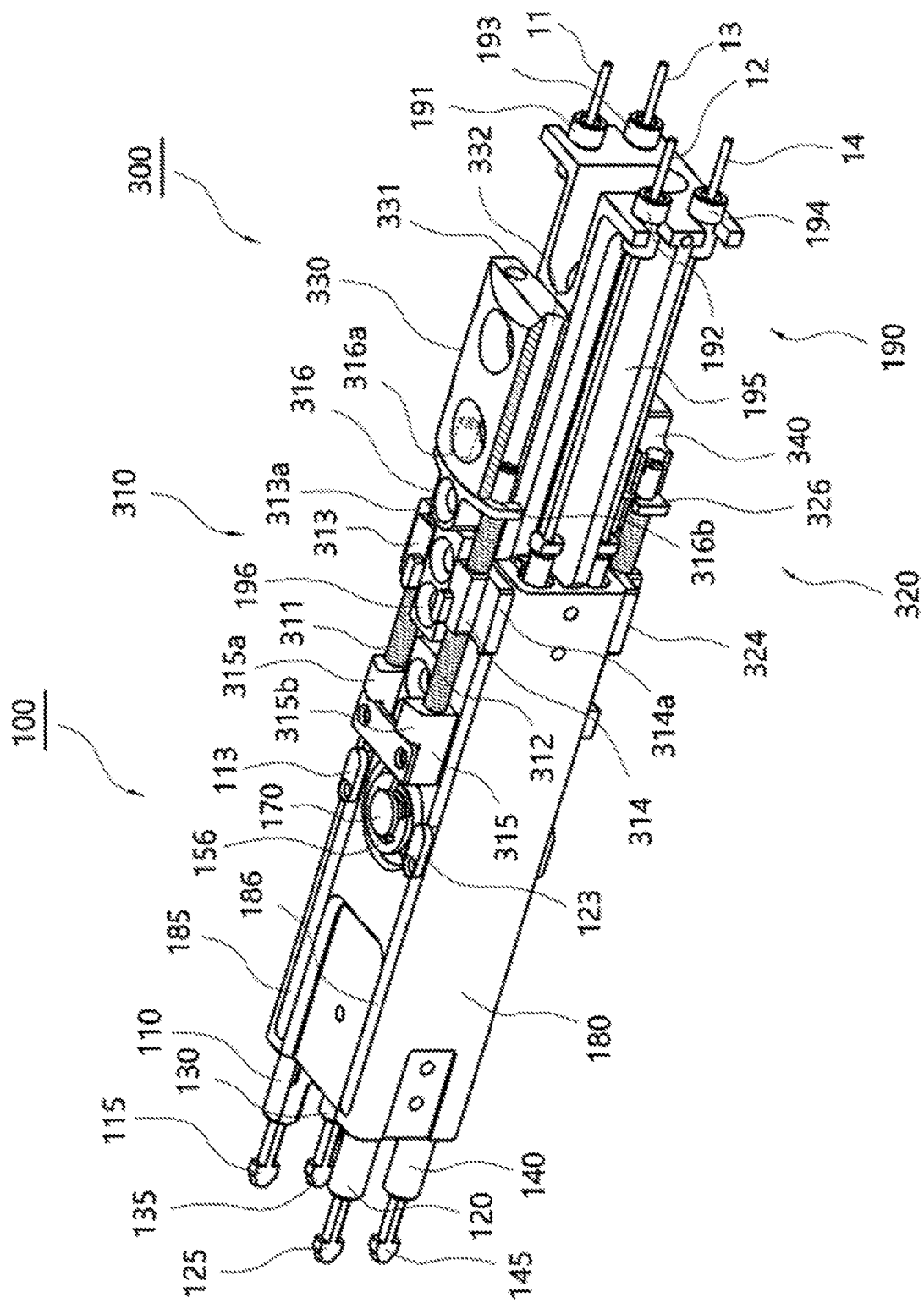
FIGS. 4a and 4b are perspective diagrams illustrating a first detachable module and a bending control part of the detachable unit provided in the detachable endoscope with the adjustable bending angle according to the exemplary embodiment of the present disclosure.
Figure 4B:
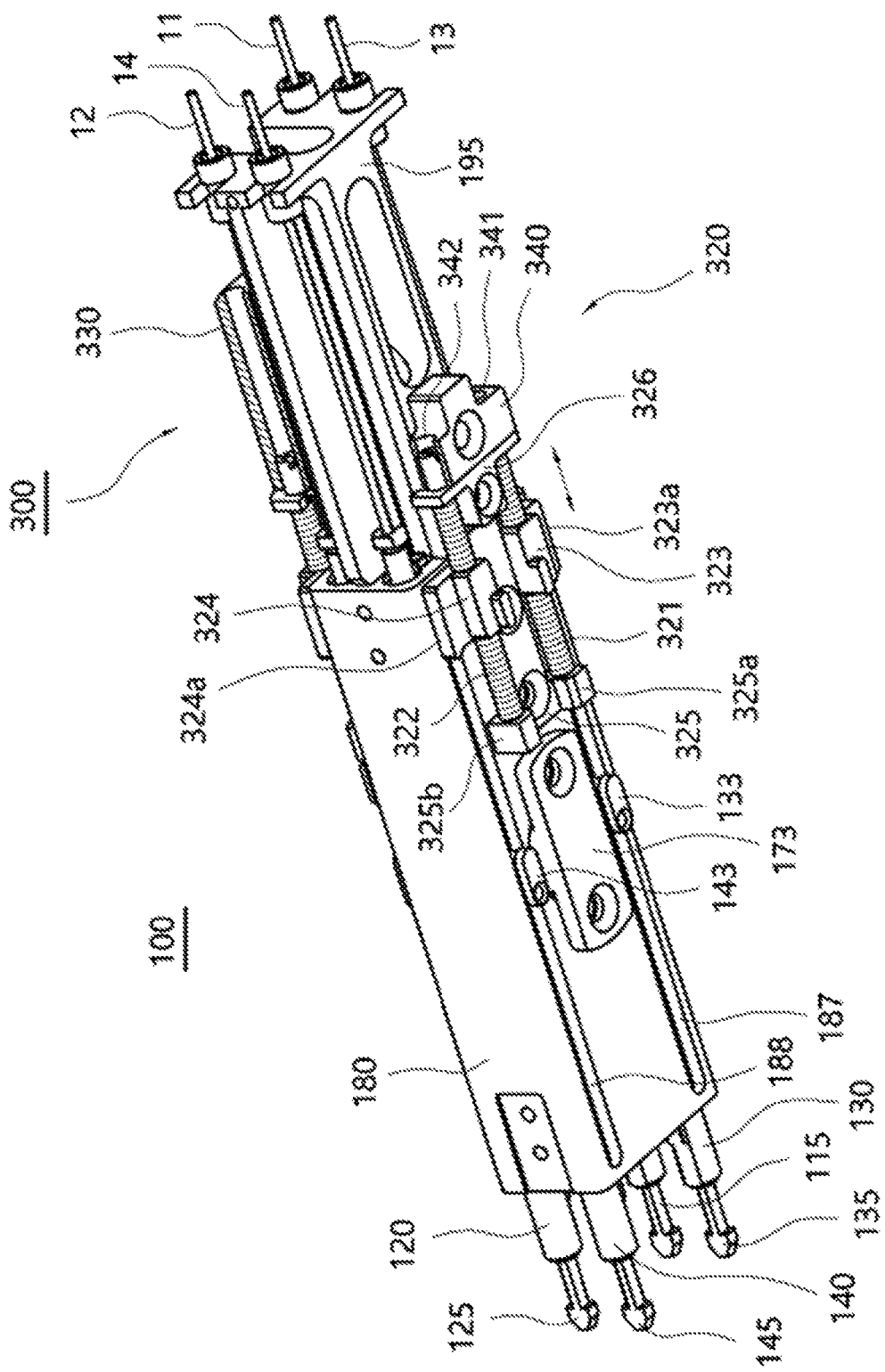
Figure 5:
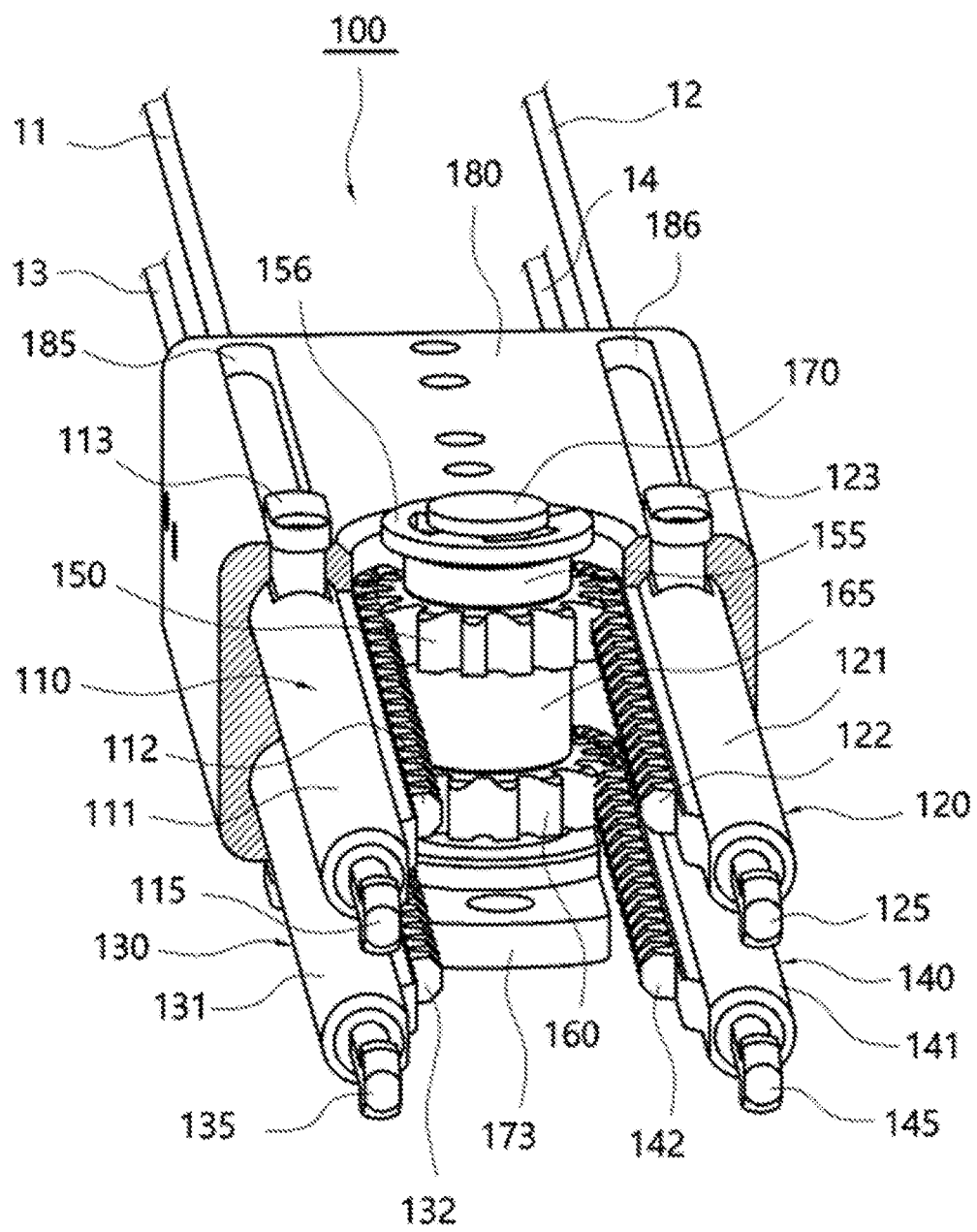
FIG. 5 is a cross-sectional perspective diagram illustrating a first detachable module of the detachable unit provided in the detachable endoscope with the adjustable bending angle according to the exemplary embodiment of the present disclosure.
Figure 6:
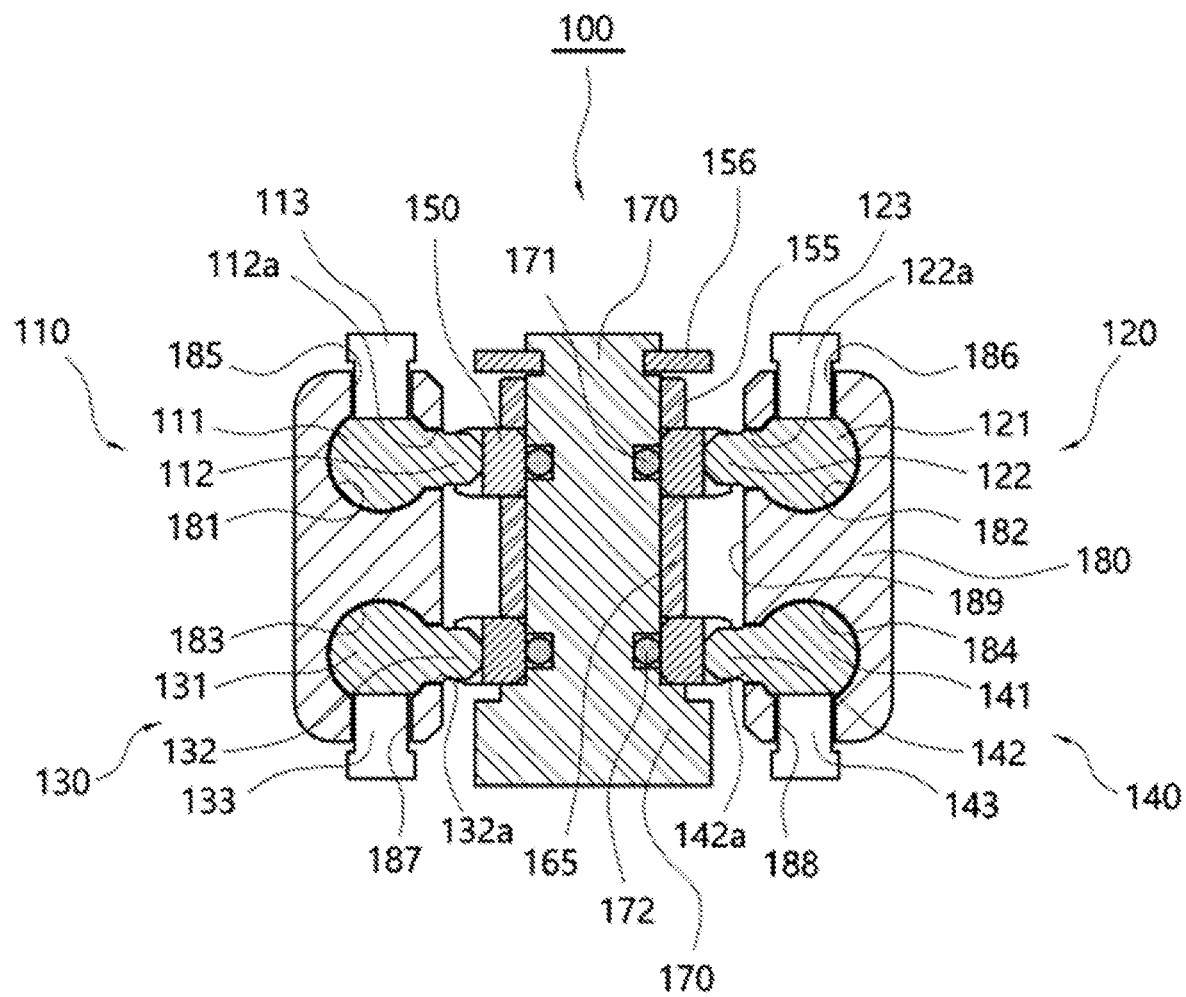
FIG. 6 is a longitudinal cross-sectional diagram illustrating the first detachable module of the detachable unit provided in the detachable endoscope with the adjustable bending angle according to the exemplary embodiment of the present disclosure.
Figure 7:
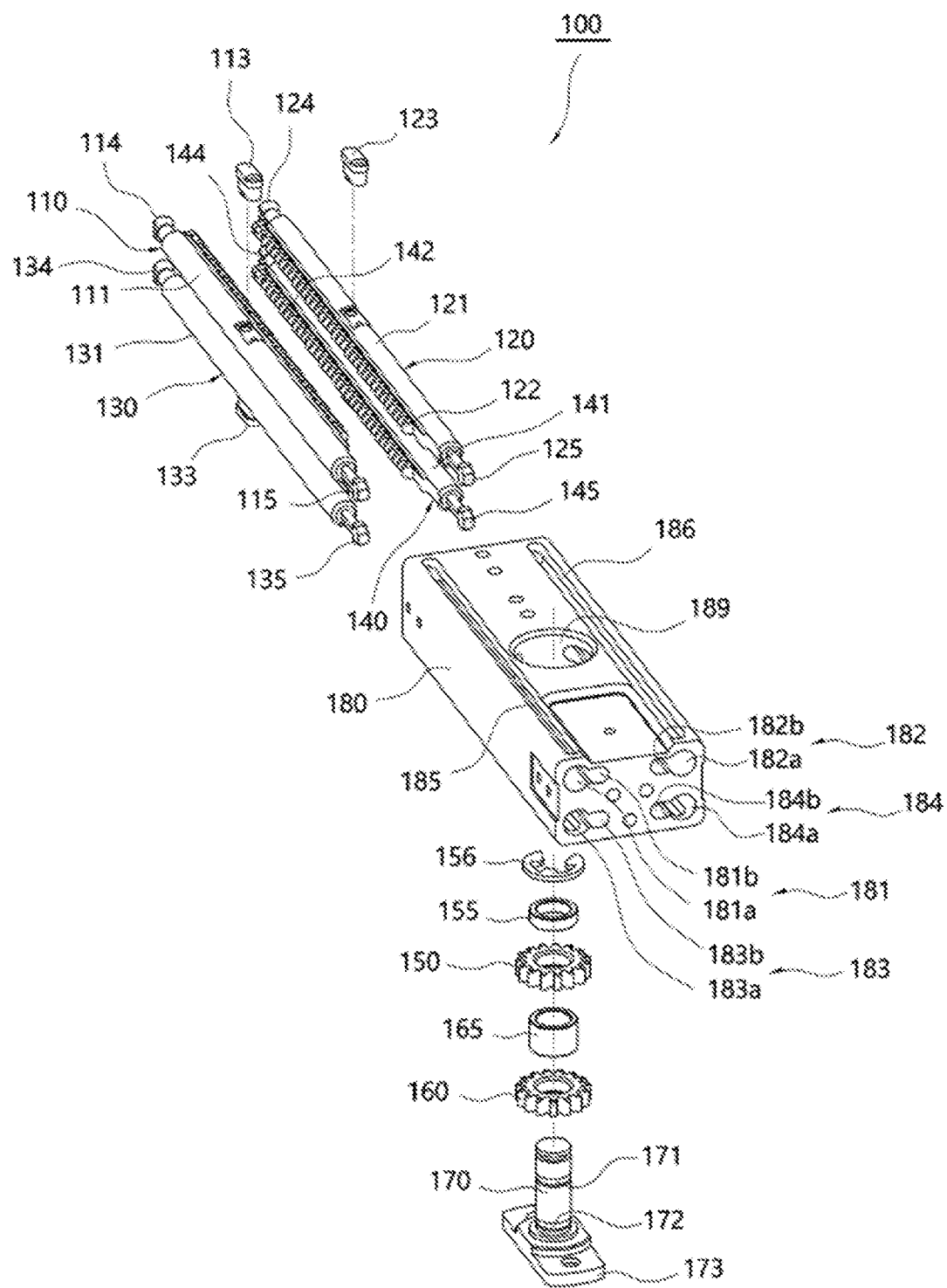
FIG. 7 is an exploded perspective diagram illustrating the first detachable module of the detachable unit provided in the detachable endoscope with the adjustable bending angle according to the exemplary embodiment of the present disclosure.
Figure 8:
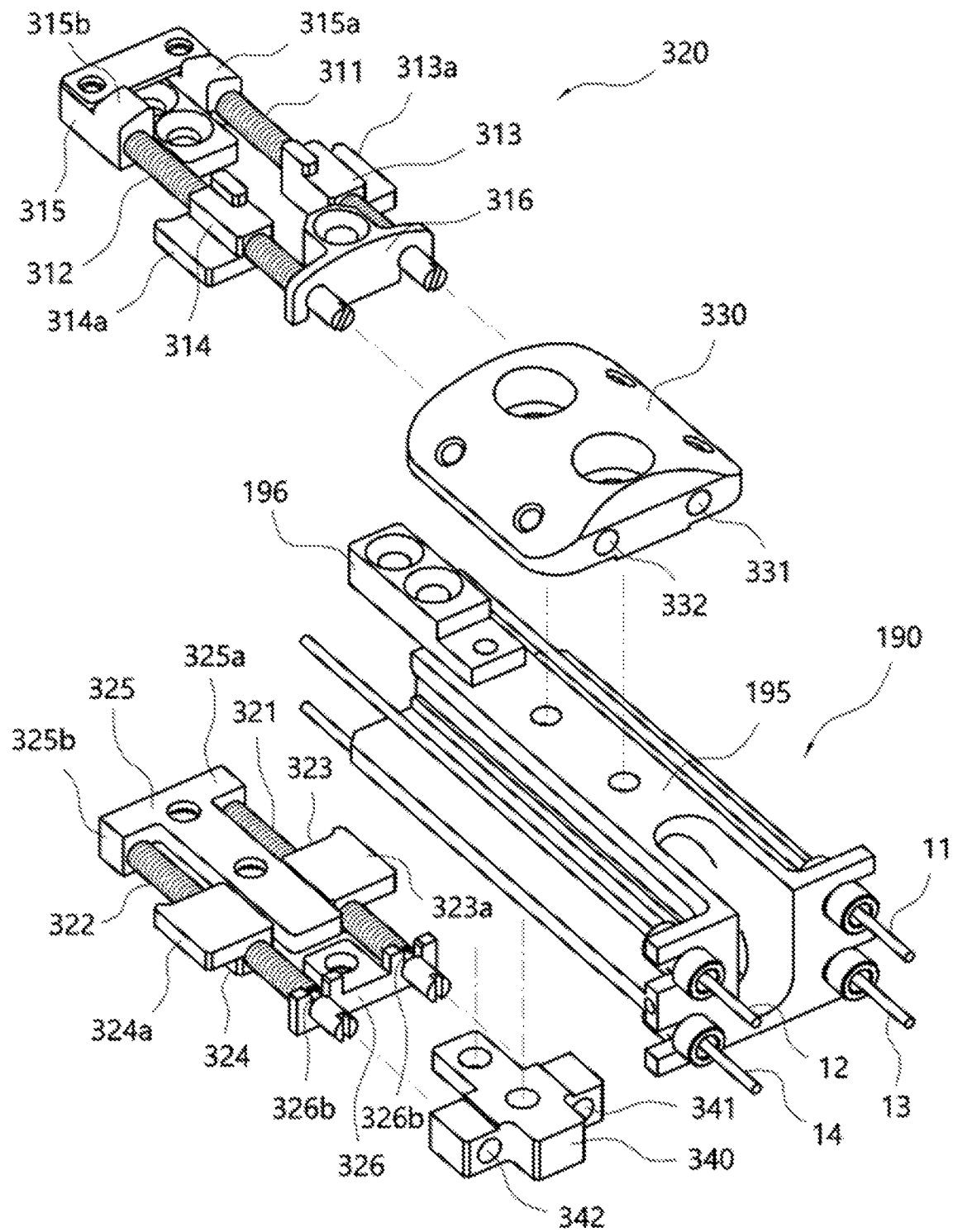
FIG. 8 is an exploded perspective diagram illustrating the bending control part of the detachable unit provided in the detachable endoscope with the adjustable bending angle according to the exemplary embodiment of the present disclosure.

In addition, as illustrated in FIGS. 4A, 4B, and 8, the first detachable module 100 includes a wire support part 190 for supporting the linear movements of the first, second, third, and fourth operation wires 11, 12, 13, 14 coupled to one ends of the first, second, third, and fourth rack gears.

The wire support part 190 has first, second, third, and fourth support bodies 191, 192, 193, 194 having support holes, into which the first, second, third, and fourth operation wires 11, 12, 13, 14 are correspondingly inserted, formed to penetrate the insides thereof, a support block 195 for fixedly installing the first, second, third, and fourth support bodies on one end thereof, and a connection bracket 196 for detachably assembling the support block 195 to one end of the first module main body 180 by a plurality of fastening members.

The first, second, third, and fourth support bodies 191, 192, 193, 194 have the support holes formed to penetrate the centers of the bodies, are formed of cylindrical members having annular grooves recessed in the outer surfaces thereof, and one end of the support block 195 has a plurality of fitting and fixing pieces, into which the grooves formed on the respective outer surfaces of the first, second, third, and fourth support bodies are correspondingly inserted and fixed.

The first detachable module 100 having the above configuration has the respective front ends of the first, second, third, and fourth connecting ports corresponding to the second detachable module of the operation part located on the same vertical surface in an initial standby state where the first and second pinion gears 150, 160 are located on the centers of the lengths of the first, second, third, and fourth rack gears 110, 120, 130, 140.

In this state, when the first detachable module provided on the rear end of the insertion part and the second detachable module provided on the front end of the operation part are coupled to each other, the first, second, third, and fourth connecting ports 115, 125, 135, 145 provided in the first, second, third, and fourth rack gears 110, 120, 130, 140 of the first detachable module and the first, second, third, and fourth connected ports 215, 225, 235, 245 of the first, second, third, and fourth connection shafts 210, 220, 230, 240 of the second detachable module 200 are locked and connected to each other.

In addition, in the state where the first, second, third, and fourth connecting ports 115, 125, 135, 145 and the first, second, third, and fourth connected ports 215, 225, 235, 245 are locked and connected to each other, when the first rack gear is moved by a predetermined distance in the left direction in the figure by the forward rotation of the upper operation handle 28 provided in the operation part, the second rack gear may be linearly moved by the same predetermined distance in the right direction, which is the opposite direction, to quantitatively pull and move the first operation wire and to quantitatively push and move the second operation wire by the gear-engagement between the first and second rack gears and the first pinion gear, thereby operating the front end of the insertion part to be bent upward at a predetermined angle in proportion to the forward rotation amount of the upper operation handle 28.

Conversely, when the second rack gear is moved by a predetermined distance in the left direction in the figure by the reverse rotation of the upper operation handle 28, the first rack gear may be linearly moved by the same predetermined distance in the right direction, which is the opposite direction, to quantitatively pull and move the second operation wire and to quantitatively push and move the first operation wire by the gear-engagement between the first and second rack gears and the first pinion gear, thereby operating the front end of the insertion part to be bent downward at a predetermined angle in proportion to the reverse rotation amount of the upper operation handle 28.

In addition, the operation of operating the front end of the insertion part to be bent horizontally at a predetermined angle by linearly moving the third and fourth rack gears by predetermined distances in opposite directions by the forward or reverse rotation of the lower operation handle 29 provided in the operation part to pull and move or push and move the third and fourth operation wires in opposite directions is the same as the linear movements of the first and second rack gears, so that a description thereof will be omitted.

Therefore, the endoscopic surgery may be performed, which removes or cures a lesion site by the treatment tool entering the insertion part while illuminating, photographing, and confirming the lesion site in the body by operating the front end of the insertion part inserted into the body to be bent vertically and horizontally by the selective rotational operations of the upper and lower operation handles provided in the operation part upon endoscopic surgery.

Meanwhile, as illustrated in FIGS. 3, 4A, 4B, and 8, the bending control part 300 includes a first adjustment part 310 and a second adjustment part 320 for adjusting the bending angle of the front end of the insertion part 10 bent and displaced vertically or horizontally before endoscopic surgery according to surgery conditions of the endoscope such as a colonofiberscope or a gastric endoscope before the endoscopic surgery.

The first adjustment part 310 may control linear movement distances of the first and second rack gears reciprocating along the first and second linear guide holes 181, 182 of the first module main body 180 upon selective rotational operation by the upper operation handle of the operation part, thereby varying the bending angle at which the front end of the insertion part is horizontally bent and displaced by the external forces transferred to the first and second operation wires 11, 12.

The first adjustment part 310 includes a first upper fixing block 315 for rotatably supporting the respective one ends of the first and second control shafts 311, 312 having predetermined lengths disposed parallel to the first and second rack gears 110, 120, a second upper fixing block 316 for rotatably supporting the respective other ends of the first and second control shafts 311, 312, and first and second stoppers 313, 314 screw-coupled to the respective outer surfaces of the first and second control shafts and provided to be movable in location so that one ends of the first and second stoppers are located on the movement paths of the first and second movable bodies 113, 123 moved together with the first and second rack gears.

Here, the first upper fixing block 315 is a block structure which is assembled and fixedly installed on the upper surface of the first module main body 180 corresponding to the first and second rack gears by the fastening member, and the second upper fixing block 316 is a block structure which is fixedly installed on one side of the upper surface of the first module main body 180 at a predetermined interval from the first upper fixing block 315.

The first and second control shafts 311, 312 are screw members having predetermined lengths which have one ends rotatably assembled via rotational support parts 315*a*, 315*b* such as bearing members provided on both ends of the first upper fixing block, and are rotatably supported by other rotational support parts 316*a*, 316*b* formed to penetrate both ends of the second upper fixing block.

The first and second stoppers 313, 314 include main bodies having female screw parts, which are screw-coupled to male screw parts formed on the outer surfaces of the first and second control shafts, formed to penetrate the insides thereof, and the respective one side ends of the main bodies have protrusions 313*a*, 314*a* formed to protrude therefrom, in which the protrusions limit the pulling movements of the first and second operation wires while selectively contacting the first and second movable bodies 113, 123 reciprocating along the first and second linear-type slits formed to be cutout on the upper surface of the first module main body.

The respective one ends of the first and second control shafts 311, 312 extending to the outside through the rotational support parts 316*a*, 316*b* of the second upper fixing block 316 are preferably formed with straight or cross-shaped grooves so as to facilitate the rotational operation by a tool.

Meanwhile, the first adjustment part 310 includes an upper auxiliary block 330 having the first and second guide holes 331, 332 formed to penetrate the inside thereof so as to perform the rotational operations of the first and second control shafts more easily, in which the respective one ends of the first and second control shafts enter and are disposed in the first and second guide holes 331, 332.

The upper auxiliary block 330 is fixedly installed on the upper surface of the support block 195 of the wire support part 190, thereby allowing a tool such as a screw driver to enter through the first and second guide holes formed to penetrate the upper auxiliary block, and then rotates a tool, which has the front end contacting the straight or cross-shaped grooves formed in the respective one ends of the first and second control shafts, in a forward or reverse direction, thereby easily performing the work of moving the locations of the first and second stoppers 313, 314 to be relatively close to or away from the first and second movable bodies.

In addition, the second adjustment part 320 may control linear movement distances of the third and fourth rack gears reciprocating along the third and fourth linear guide holes 183, 184 of the first module main body 180 upon selective rotational operation by the lower operation handle of the operation part, thereby varying the angle at which the front end of the insertion part is vertically bent and displaced by the external forces transferred to the third and fourth operation wires 13, 14.

The second adjustment part 320 includes a first lower fixing block 325 for rotatably supporting the respective one ends of the third and fourth control shafts 321, 322 having predetermined lengths disposed parallel to the third and fourth rack gears 130, 140, a second lower fixing block 326 for rotatably supporting the respective other ends of the third and fourth control shafts 321, 322, and third and fourth stoppers 323, 324 screw-coupled to the respective outer surfaces of the third and fourth control shafts and provided to be movable in location so that one ends of the third and fourth stoppers are located on the movement paths of the third and fourth movable bodies 133, 143 moved together with the third and fourth rack gears.

Here, the first lower fixing block 325 is a block structure which is assembled and fixedly installed on the lower surface of the first module main body 180 corresponding to the third and fourth rack gears by the fastening member, and the second lower fixing block 326 is a block structure which is fixedly installed on one side of the lower surface of the first module main body 180 at a predetermined interval from the first lower fixing block 325.

The third and fourth control shafts 321, 322 are screw members having predetermined lengths which have one ends rotatably assembled via rotational support parts 325a, 325b such as bearing members provided on both ends of the first lower fixing block, and are rotatably supported by other rotational support parts 326a, 326b formed to penetrate both ends of the second lower fixing block.

The third and fourth stoppers 323, 324 include main bodies having female screw parts, which are screw-coupled to male screw parts formed on the outer surfaces of the third and fourth control shafts, formed to penetrate the insides thereof, and the respective one side ends of the main bodies have protrusions 323a, 324a formed to protrude therefrom, in which the protrusions limit the pulling movements of the third and fourth operation wires while selectively contacting the third and fourth movable bodies 133, 143 reciprocating along the third and fourth linear-type slits 187, 188 formed to be cutout on the lower surface of the first module main body.

The respective one ends of the third and fourth control shafts 321, 322 extending to the outside through the rotational support parts 326a, 326b of the second lower fixing block 326 are preferably formed with straight or cross-shaped grooves so as to facilitate the rotational operation by a tool.

Meanwhile, the second adjustment part 320 includes a lower auxiliary block 340 having the third and fourth guide holes 341, 342 formed to penetrate the inside thereof so as to perform the rotational operations of the third and fourth control shafts more easily, in which the respective one ends of the third and fourth control shafts enter and are disposed in the third and fourth guide holes 341, 342.

The lower auxiliary block 340 is fixedly installed on the lower surface of the support block 195 of the wire support part 190, thereby allowing a tool such as a screw driver to enter through the third and fourth guide holes formed to penetrate the lower auxiliary block, and then rotates a tool, which has the front end contacting the straight or cross-shaped grooves formed in the respective one ends of the third and fourth control shafts, in a forward or reverse direction, thereby easily performing the work of moving the locations of the third and fourth stoppers 323, 324 to be relatively close to or away from the third and fourth movable bodies.

It is possible to easily and precisely adjust the maximum value of the bending angle at which the front end of the insertion part 10 is bent vertically, and the maximum value of the bending angle at which the front end of the insertion part 10 is bent horizontally by the selective rotational operation of the operation part using the first adjustment part 310 and the second adjustment part 320 of the bending control part 300 having the above configuration according to the surgery conditions such as the gastric endoscopic surgery or the colonofiberscope surgery.

That is, by rotationally operating the first and second control shafts 311, 312 in a forward or reverse direction using a tool such as a screw driver entering through the first and second guide holes of the upper auxiliary block 330, the first and second stopper 313, 314 may vary a movement limit distance (L) formed between the first and second movable bodies and the first and second stoppers while reciprocating in a section corresponding between the first upper fixing block and the second upper fixing block in proportion to the rotational amounts of the first and second control shafts.

Figure 9A:
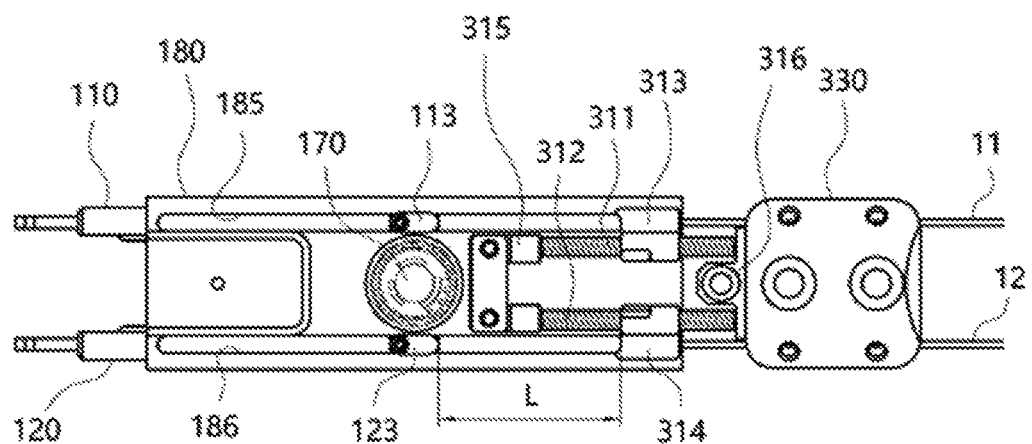
FIGS. 9*a*, 9*b*, and 9*c* are diagrams illustrating operation states of the bending control part provided in the detachable endoscope with the adjustable bending angle according to the exemplary embodiment of the present disclosure.

Here, as illustrated in FIG. 9a, the movement limit distance (L) is a straight distance measured between the locations of the first and second movable bodies 113, 123 upon standby and stop of the first detachable module and the locations of the first and second stoppers movably assembled in the first and second control shafts.

Figure 9B:
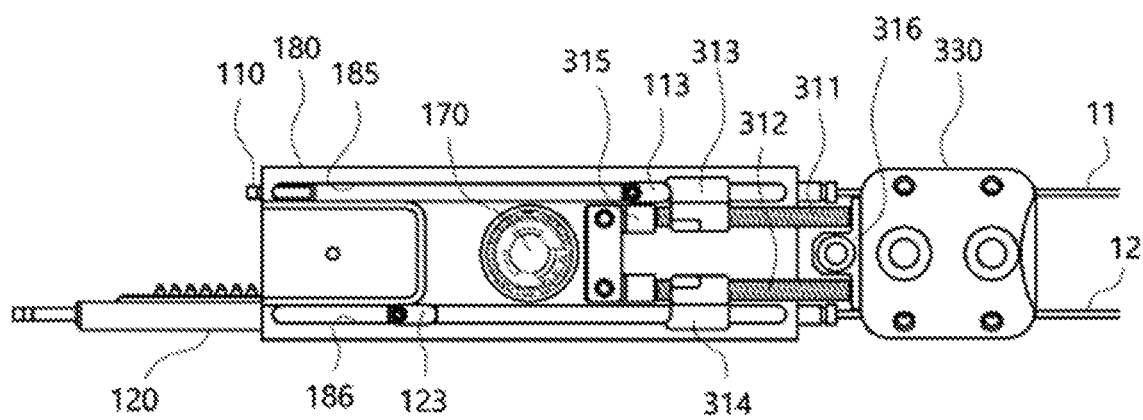

When the locations of the first and second stoppers 313, 314 are moved to the left in the figure so as to be close toward the first and second movable bodies and thus a movement limit distance (L) therebetween is shortened, as illustrated in FIG. 9b, the movement distances of the first and second movable bodies linearly moving along the first and second linear-type slits 185, 186 by the selective rotational operation of the operation part and the movement distances of the first and second operation wires pulled or pushed in conjunction therewith may be shortened, thereby setting the bending angle for operating the front end of the insertion part to be bent vertically as a small angle according to the colonofiberscope surgery conditions.

Figure 9C:
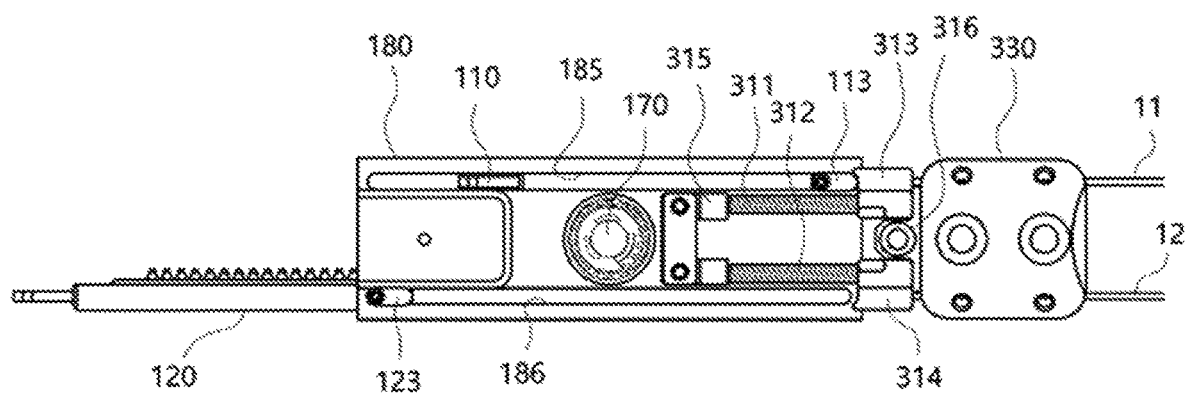

On the other hand, when the locations of the first and second stoppers 313, 314 are moved to the right in the figure so as to be away from the first and second movable bodies and thus the movement limit distance therebetween is lengthened, as illustrated in FIG. 9C, the movement distances of the first and second movable bodies linearly moving along the first and second linear-type slits 185, 186 by the selective rotational operation of the operation part and the movement distances of the first and second operation wires pulled or pushed in conjunction therewith may be lengthened, thereby setting the bending angle for operating the front end of the insertion part to be bent vertically as a large angle according to the gastric endoscope surgery conditions.

At this time, although it has been illustrated and described that the locations of the first and second stoppers 313, 314 for controlling the movement distances at which the first and second operation wires 11, 12 are pulled by contacting the first and second movable bodies 113, 123 are moved to form the same movement limit distances (L) so as to operate the front end of the insertion part to be bent vertically at the same bending angles, the present disclosure is not limited thereto and the locations of the first and second stoppers may be independently moved, respectively so as to form different movement limit distances.

That is, when the stop location of the first stopper and the stop location of the second stopper are set differently from each other, the movement limit distances until the first and second movable bodies contact the first and second stoppers to stop may be set differently from each other, thereby variously setting the bending angle at which the front end of the insertion part is bent upward or downward by the selective rotational operation of the operation part in the gastric endoscope surgery conditions and the colonofiberscope surgery conditions, respectively.

Meanwhile, the third and fourth control shafts 321, 322 are rotationally operated in a forward or reverse direction using a tool such as a screw driver entering through the third and fourth guide holes of the lower auxiliary block 340.

Since the fact that the locations of the third and fourth stoppers 323, 324 are moved in the section corresponding between the first lower fixing block and the second lower fixing block in proportion to the rotational amounts of the third and fourth control shafts by the rotational operation, thereby varying the movement limit distance (L) formed between the third and fourth movable bodies and the third and fourth stoppers, and the maximum horizontal bending angle of the front end of the insertion part is adjusted according to the surgery conditions such as the gastric endoscope surgery or the colonofiberscope surgery by varying the movement limit distances is the same as the operation of the first adjustment part, a description thereof will be omitted.

In addition, although it has been illustrated and described that the first, second, third, and fourth control shafts of the first and second adjustment parts are manually operated using the tool such as the screw driver entering the upper and lower auxiliary blocks, they are not limited thereto and the respective one ends of the first, second, third, and fourth control shafts may be precisely controlled by a drive motor for generating a rotational driving force upon applying power.

The aforementioned present disclosure is not limited to the aforementioned exemplary embodiments and the accompanying drawings, and it will be apparent to those skilled in the art to which the present disclosure pertains that various substitutions, modifications, and changes are possible without departing from the technical spirit of the present disclosure.

The invention claimed is:

1. A detachable endoscope comprising:
an operation part for operating a front end of an insertion part to be bent; and
a detachable unit for detachably coupling the operation part and the insertion part,
wherein the detachable unit comprises:
a first detachable module connected to operation wires that are connected to the front end of the insertion part;
a second detachable module connected to connection wires of a direction conversion part for converting a rotational motion into a linear motion in the operation part; and
a bending control part for adjusting an angle of the front end of the insertion part,
wherein the first detachable module comprises:
a first module main body having linear guide holes formed in a longitudinal direction thereof, and having a central placement hole formed in a thickness direction thereof;
a plurality of rack gears connected to the operation wires and disposed in the linear guide holes;
a first pinion gear engaged between first and second rack gears of the plurality of rack gears;
a second pinion gear engaged between third and fourth rack gears of the plurality of rack gears; and
a gear shaft disposed in the central placement hole, the first and second pinion gears being assembled with the gear shaft,
wherein the bending control part comprises:
a first adjustment part for controlling linear movement distances of the first and second rack gears to adjust a vertical bending angle of the front end of the insertion part; and
a second adjustment part for controlling linear movement distances of the third and fourth rack gears to adjust a horizontal bending angle of the front end of the insertion part,
wherein the first adjustment part comprises:
first and second control shafts disposed parallel to the first and second rack gears; and
first and second stoppers assembled with the first and second control shafts to be movable such that one ends thereof are located on movement paths of first and second movable bodies moving with the first and second rack gears.

2. The detachable endoscope of claim 1,
wherein the first adjustment part further comprises:
a first upper fixing block for rotatably supporting one ends of first and second control shafts; and
a second upper fixing block for rotatably supporting another ends of the first and second control shafts.

3. The detachable endoscope of claim 2,
wherein the first and second stoppers comprise:
first and second main bodies; and
protrusions protruding from one side ends of the first and second main bodies screw-coupled to outer surfaces of the first and second control shafts so as to contact the first and second movable bodies reciprocating along first and second linear-type slits of the first module main body.

4. The detachable endoscope of claim 2,
wherein one side ends of the first and second control shafts have straight or cross-shaped grooves so as to facilitate a locking rotational operation by a tool.

5. The detachable endoscope of claim 4,
wherein the first adjustment part further comprises an upper auxiliary block having first and second guide holes, in which the one ends of the first and second control shafts are disposed.

6. The detachable endoscope of claim 1,
wherein the second adjustment part comprises:
a first lower fixing block for rotatably supporting one ends of third and fourth control shafts disposed parallel to the third and fourth rack gears;
a second lower fixing block for rotatably supporting another ends of the third and fourth control shafts; and
third and fourth stoppers assembled with the third and fourth control shafts to be movable such that one ends thereof are located on movement paths of third and fourth movable bodies moving with the third and fourth rack gears.

7. The detachable endoscope of claim 6,
wherein the third and fourth stoppers comprise:
third and fourth main bodies; and
protrusions formed protruding from one side ends of the third and fourth main bodies screw-coupled to outer surfaces of the third and fourth control shafts so as to contact the third and fourth movable bodies reciprocating along third and fourth linear-type slits of the first module main body.

8. The detachable endoscope of claim 6,
wherein one side ends of the third and fourth control shafts have straight or cross-shaped grooves so as to facilitate a locking rotational operation by a tool.

9. The detachable endoscope of claim 8,
wherein the second adjustment part further comprises a lower auxiliary block having third and fourth guide holes, in which the one ends of the third and fourth control shafts are disposed.

* * * * *